United States Patent
Savary

(10) Patent No.: US 10,398,652 B2
(45) Date of Patent: Sep. 3, 2019

(54) SODIUM BICARBONATE PARTICLES MANUFACTURED BY ATOMIZATION

(71) Applicant: SOLVAY SA, Brussels (BE)

(72) Inventor: David Jean Lucien Savary, Dombasle-sur-Meurthe (FR)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 14/653,616

(22) PCT Filed: Dec. 23, 2013

(86) PCT No.: PCT/EP2013/077948
§ 371 (c)(1),
(2) Date: Jun. 18, 2015

(87) PCT Pub. No.: WO2014/096457
PCT Pub. Date: Jun. 26, 2014

(65) Prior Publication Data
US 2015/0359745 A1  Dec. 17, 2015

Related U.S. Application Data

(60) Provisional application No. 61/745,227, filed on Dec. 21, 2012.

(51) Int. Cl.
*A61K 9/16* (2006.01)
*A61K 33/00* (2006.01)
*C01D 7/12* (2006.01)
*C01D 7/38* (2006.01)

(52) U.S. Cl.
CPC .......... *A61K 9/1682* (2013.01); *A61K 9/1611* (2013.01); *A61K 9/1617* (2013.01); *A61K 33/00* (2013.01); *C01D 7/123* (2013.01); *C01D 7/38* (2013.01)

(58) Field of Classification Search
CPC .... A61K 9/1682; A61K 33/00; A61K 9/1617; A61K 9/1611; C01D 7/123; C01D 7/38
See application file for complete search history.

(56) References Cited

U.S. PATENT DOCUMENTS

| | | |
|---|---|---|
| 3,037,849 A | 6/1962 | Frint et al. |
| 3,072,466 A | 1/1963 | Bauer et al. |
| 3,233,983 A | 2/1966 | Bauer et al. |
| 3,248,182 A | 4/1966 | Herink et al. |
| 5,411,750 A | 5/1995 | Lajoie et al. |
| 6,042,622 A | 3/2000 | Larsen |
| 6,660,049 B1 | 12/2003 | Day |
| 2002/0172713 A1* | 11/2002 | Einziger ............ A61K 8/0241 424/489 |
| 2007/0286790 A1 | 12/2007 | Tinson et al. |
| 2008/0032023 A1* | 2/2008 | Fonkeu ............. A23L 1/2367 426/548 |
| 2011/0027152 A1* | 2/2011 | Cui .................... C01D 7/24 423/179 |
| 2013/0095011 A1 | 4/2013 | Breton et al. |

FOREIGN PATENT DOCUMENTS

| | | |
|---|---|---|
| EP | 0623553 A1 | 11/1994 |
| GB | 532301 A | 1/1941 |
| GB | 912893 A | 12/1962 |
| JP | 2160618 A | 6/1990 |
| JP | 04270113 A | 9/1992 |
| JP | 5339005 A | 12/1993 |
| WO | WO 2011161120 | * 12/2011 |
| WO | WO 2013124652 A1 | 8/2013 |

OTHER PUBLICATIONS

Videnov—Two stage filtration of sodium bicarbonate in the manufacture of calcined soda with a surfactant addition; Godishnik na Visshiya Khimikotekhnologicheski Institut, Sofiya (1987), Volume Date 1986, 28(3), pp. 151-156—in Bulgarian language—only English Abstract provided—1 page.

* cited by examiner

*Primary Examiner* — Mina Haghighatian
(74) *Attorney, Agent, or Firm* — Beatrice C. Ortego

(57) ABSTRACT

Method for producing sodium bicarbonate particles by spray-drying of an aqueous solution comprising 1 to 10% by weight of sodium bicarbonate and an additive selected from the group consisting of: magnesium salt, sodium alkylbenzene sulfonate and soybean lecithin. Sodium bicarbonate particles obtainable by such process and comprising at least 20 mg of the additive per kg of sodium bicarbonate particles.

22 Claims, 6 Drawing Sheets

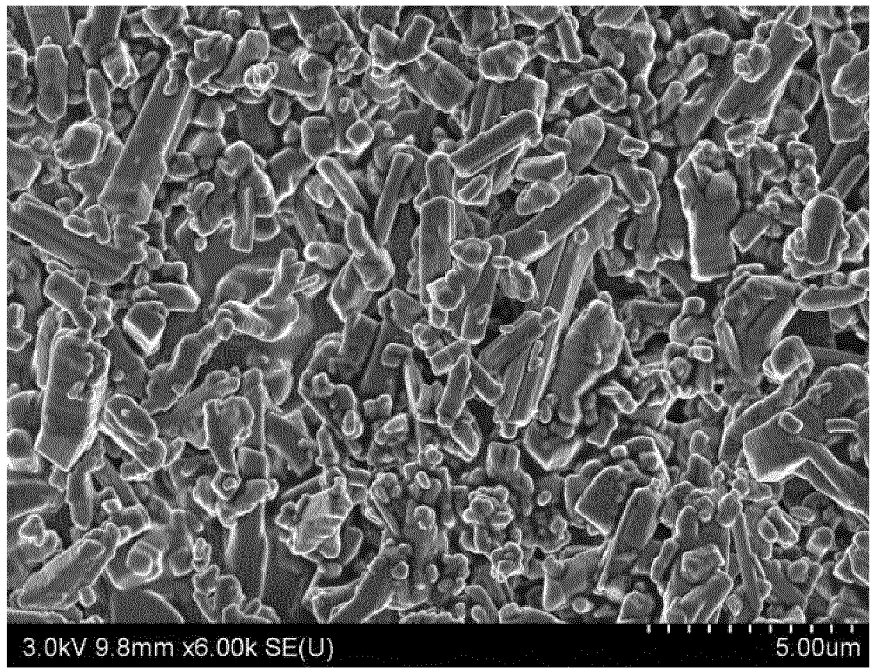
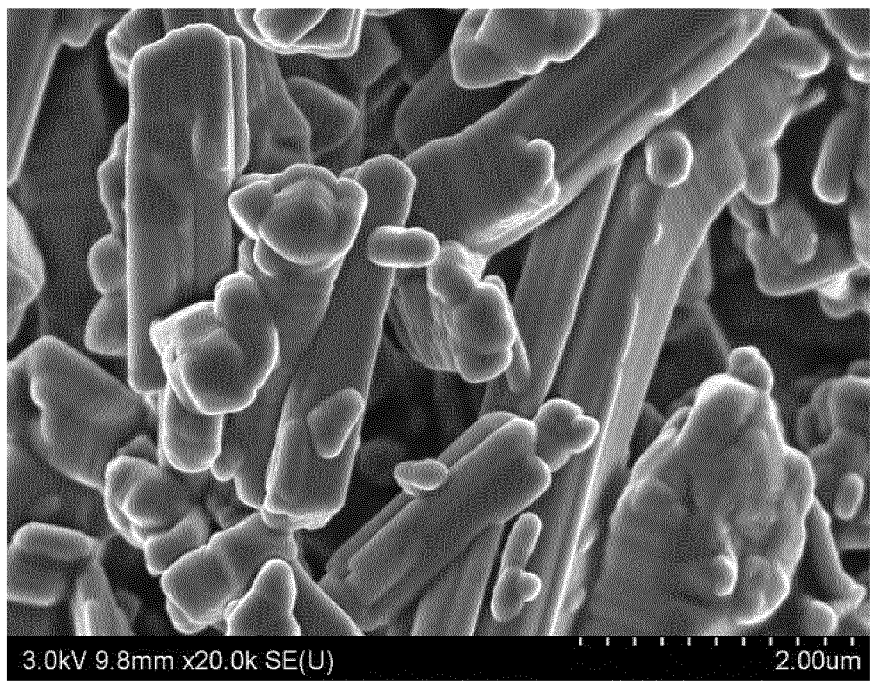
Fig.1

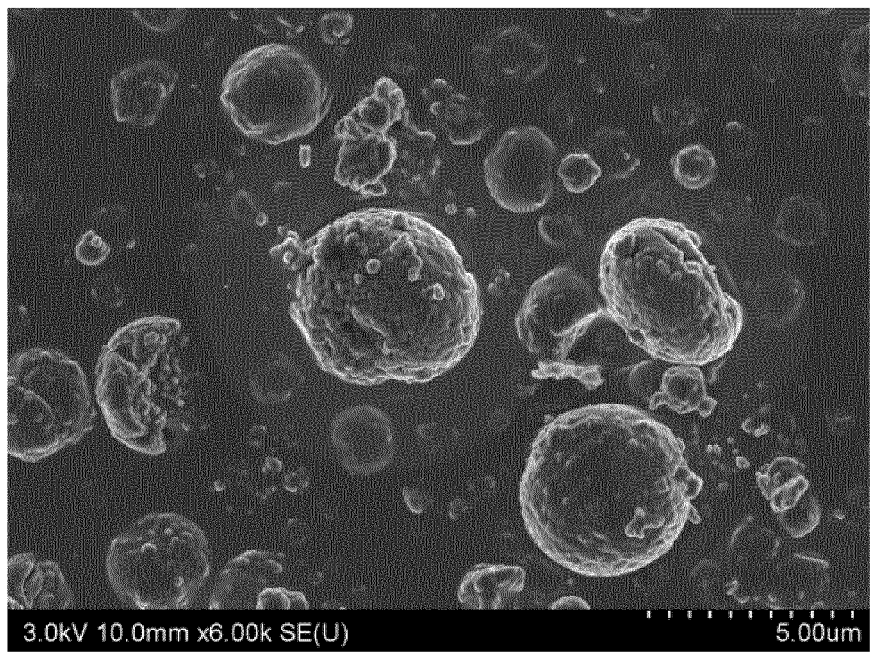
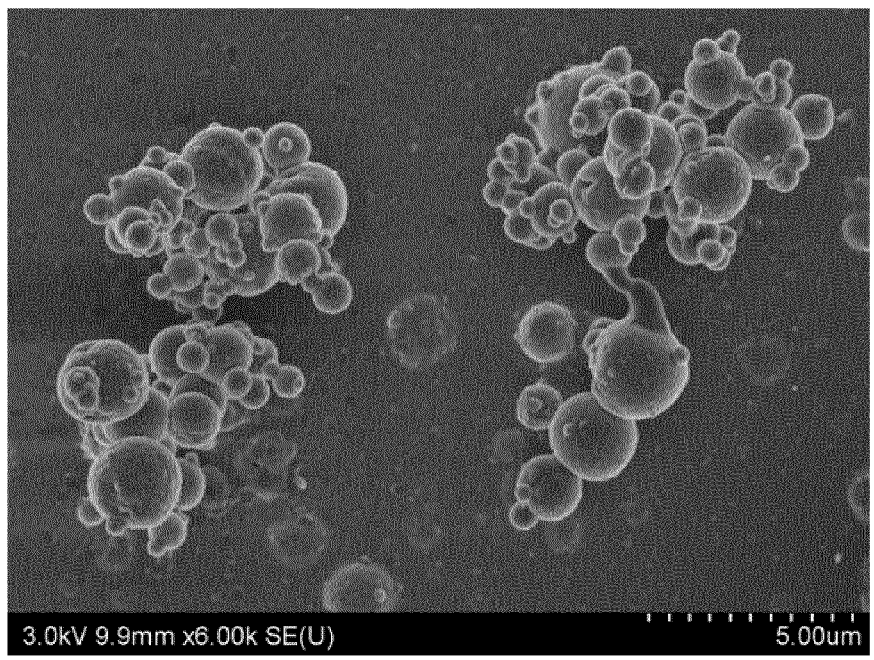
Fig.2

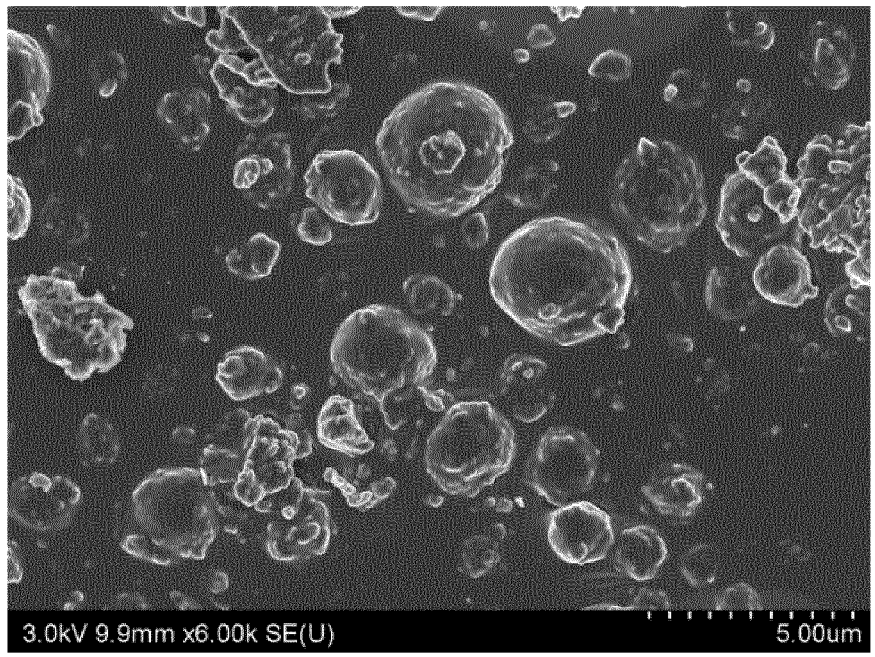
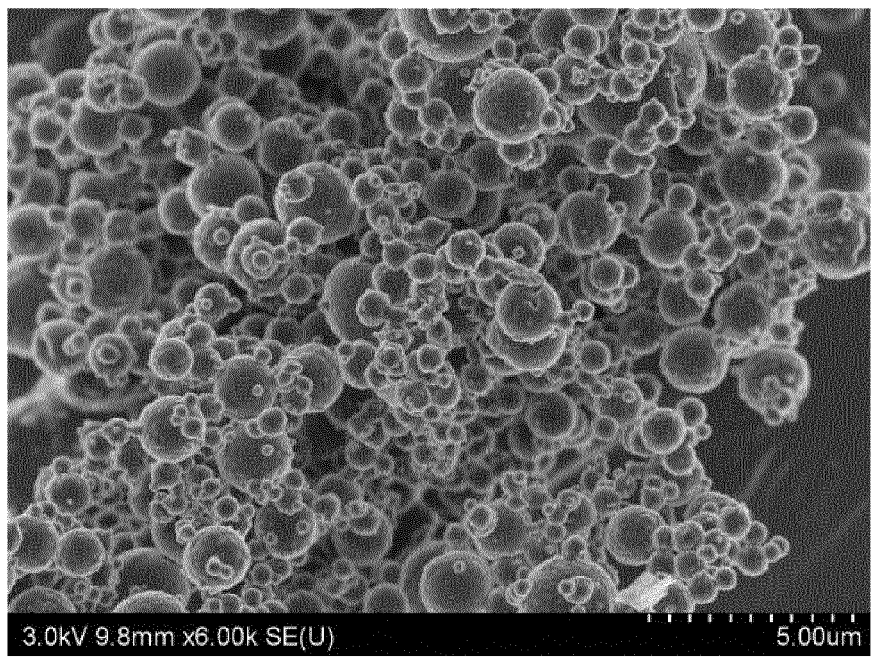
Fig.3

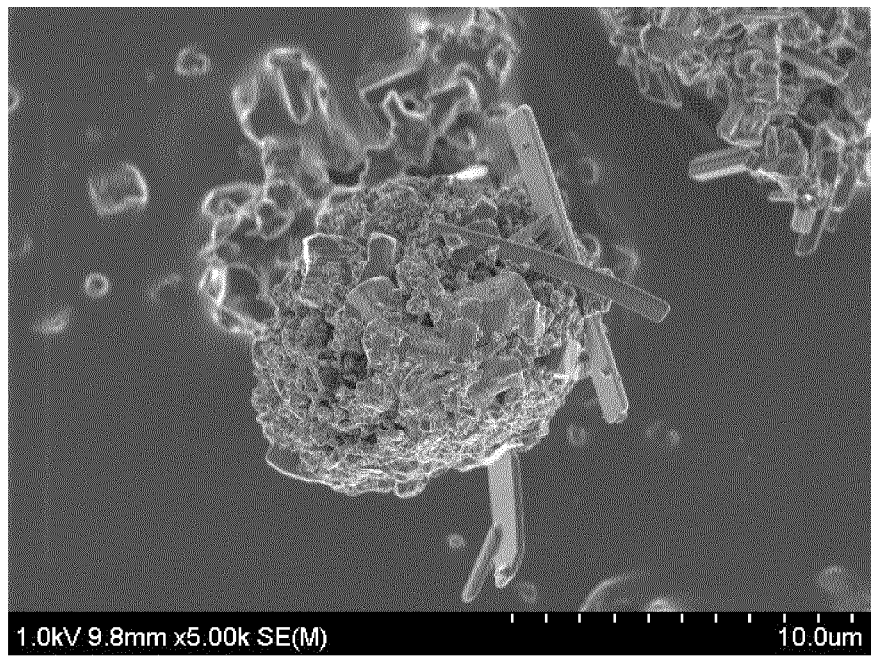
Fig.4 Ref. test - no additive
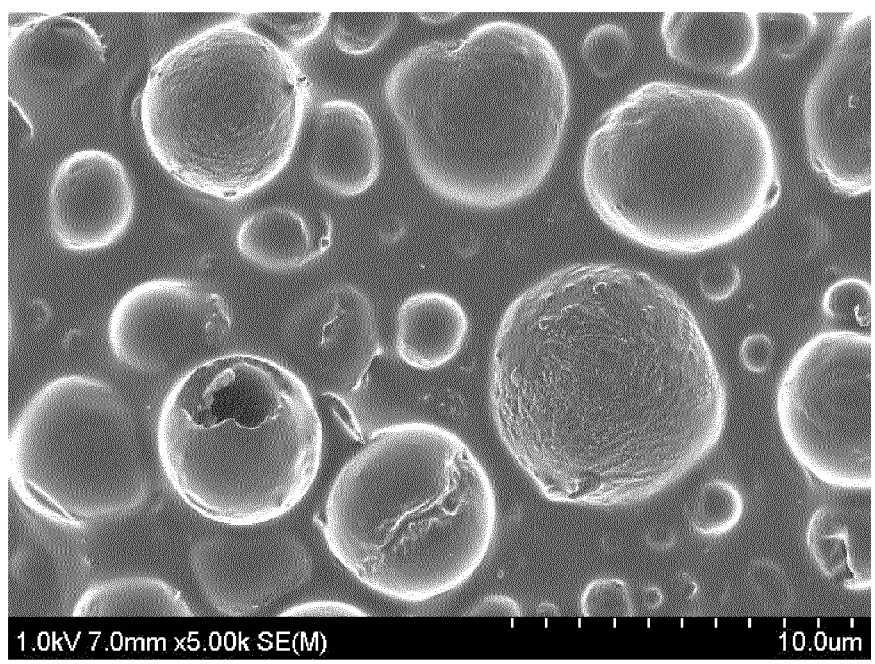
Fig.5

SODIUM BICARBONATE PARTICLES MANUFACTURED BY ATOMIZATION

CROSS-REFERENCE TO RELATED APPLICATIONS

The present application is a U.S. national stage entry under 35 U.S.C. § 371 of International Application No. PCT/EP2013/077948 filed Dec. 23, 2013, which claims priority to U.S. provisional Application No. 61/745,227 filed on Dec. 21, 2012, this application being herein incorporated by reference for all purposes.

FIELD OF THE INVENTION

The invention relates to a method for producing sodium bicarbonate by spray-drying, or atomization, of an aqueous solution comprising 1 to 10% by weight of sodium bicarbonate and an additive selected from the group consisting of: a compound of magnesium (Mg), sodium alkylbenzenesulfonate and soybean lecithin.

The invention also relates to the sodium bicarbonate particles thus produced, and to an aqueous gel comprising sodium bicarbonate particles of present invention, and also to sodium carbonate particles obtainable or obtained by calcination of sodium bicarbonate particles of present invention.

PRIOR ART

This patent relates to the drying of sodium bicarbonate by atomization, resulting in a particle size of the order of about one hundred nanometers.

Patent U.S. Pat. No. 5,411,750 describes the drying of sodium bicarbonate and potassium bicarbonate mixtures by atomization, resulting in a particle size of 100 nm-1 μm (particle size determined by transmission electron microscopy and by X-ray diffractometry) and a specific surface area of the particles obtained: 6 to 15 $m^2/g$. To obtain such small particle sizes and high specific surface area, it is used very low concentrations of bicarbonate compounds used for spray drying: 3 g $KHCO_3$/100 g $H_2O$ 3 g $NaHCO_3$/100 g $H_2O$ so respectively 0.3% for each bicarbonate compound is very low. This leads to about 99 ton of water per ton of bicarbonate to evaporate (using air at 140° C.). And so this leads to huge energy consumption per ton of bicarbonate particles produced. The document indicates that a solution containing both sodium bicarbonate and potassium bicarbonate makes it possible to obtain smaller particles than a solution of sodium bicarbonate. The document discloses that the particles obtained are cohesive agglomerated crystallites of primary particles, and is silent on the shape of such agglomerates.

The document is silent as to how to obtain sodium bicarbonate particles at lower cost when using more concentrated aqueous solution of bicarbonate salts, is silent on particles of different shape, in particular in spherical shape, with improved flowability, making it possible to obtain stable gels, and make it possible to obtain a powder with increased reactivity when it is calcined in the form of sodium carbonate The object of the present invention is to improve this type of technique and to produce novel sodium bicarbonate particles at lower cost.

BRIEF SUMMARY OF THE INVENTION

The present invention relates therefore to a method for producing sodium bicarbonate particles by spray-drying of an aqueous solution comprising 1 to 10% by weight of sodium bicarbonate and an additive selected from the group consisting of: a compound of magnesium (Mg), sodium alkylbenzene sulfonate and soybean lecithin.

It also relates to sodium bicarbonate particles produced by the method of present invention and comprising at least 20 mg of the additive per kg of sodium bicarbonate particles (when a magnesium compound expressed as: milligram of Mg).

The present invention relates also to the use of such sodium bicarbonate particles, as their particular low bulk density, the high specific surface area, their specific shape brings interesting properties of controllable dissolution speed, easy dispersing ability with gas for uses in inhalable drug applications, improved particles interface compatibility with polymers when the additive is an alkylebenzenesulfonate or soybean lecithin when the particles are used for instance as plastic blowing agent, and also high speed of calcination.

The present invention also relates to an aqueous gel comprising sodium bicarbonate particles of the invention as being stable with particularly low settling velocities, and also to sodium carbonate particles obtainable or obtained by calcination of the sodium bicarbonate particles of present invention, showing a high specific surface area and very low bulk density.

BRIEF DESCRIPTION OF THE DRAWINGS

FIG. 1: is scanning microscope views of the sodium bicarbonate particles obtained at Example 1 for a reference test without additive.

FIG. 2: is scanning microscope views of the sodium bicarbonate particles obtained at Example 2 with sodium alkylbenzenesulfonate (NaDBS) additive.

FIG. 3: is scanning microscope views of the sodium bicarbonate particles obtained at Example 3 with soybean lecithin additive.

FIG. 4: is scanning microscope views of the sodium bicarbonate particles obtained at Example 5 for a reference test without additive.

FIG. 5: is scanning microscope views of the sodium bicarbonate particles obtained at Example 6: NaDBS as additive.

DEFINITIONS

Figure 6:
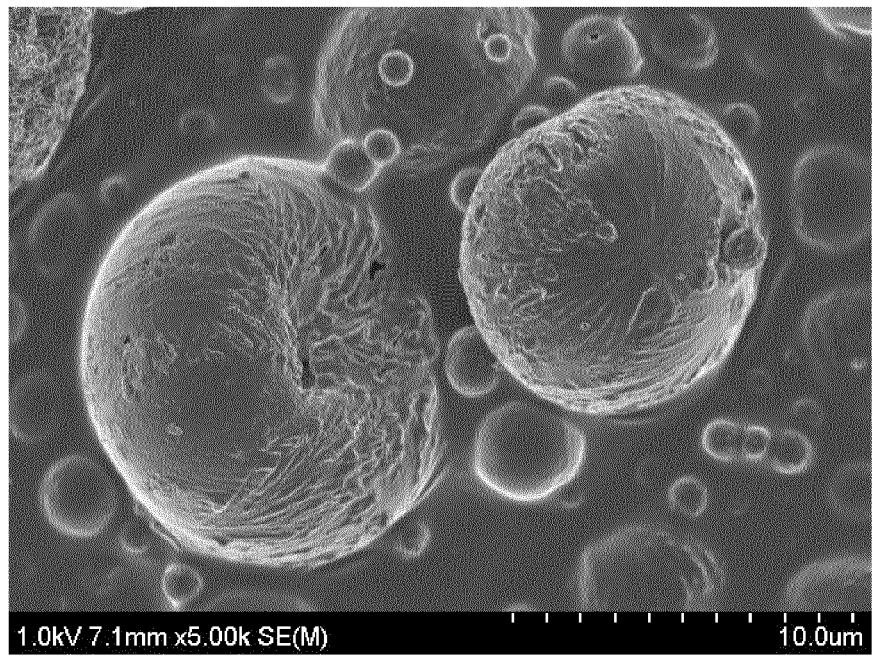
FIG. 6: is scanning microscope views of the sodium bicarbonate particles obtained at Example 7: Lecithin as additive.

In the present description, where an element or component is said to be included in and/or selected from a list of recited elements or components, it should be understood that in related embodiments explicitly contemplated here, the element or component can also be any one of the individual recited elements or components, or can also be selected from a group consisting of any two or more of the explicitly listed elements or components.

Further, it should be understood that elements and/or features of an apparatus, a process, or a method described herein can be combined in a variety of ways without departing from the scope and disclosures of the present teachings, whether explicit or implicit herein.

As used herein, the term "about" refers to a +−10% variation from the nominal value unless specifically stated otherwise.

The sign '%' refers to 'weight %' unless specifically stated otherwise.

As used herein particles 'in spherical shape' refers to particles which shape on electron scanning microscope has an ovoid shape with larger diameter to smaller diameter ratio of less than 1.4.

DETAILED DESCRIPTION OF THE INVENTION

Spray drying or drying by atomization is a drying technique. This method consists in spraying the product to be dried, which is in the form of a solution (or a suspension) in a stream of hot gas, so as to obtain a powder in a few seconds or fractions of seconds. The division of a product into fine droplets gives rise to a large material transfer surface and rapid evaporation of the solvent of the solution used.

An apparatus for drying by atomization generally comprises several modules: a module comprising a circuit for storing and atomizing the solution comprising equipments for atomizing or spraying the solution, a module for the preparation of hot gas and its transfer to a drying chamber where it comes into contact with the sprayed solution, a drying chamber where the sprayed solution is evaporated and the particles are formed, and a module for collecting the particles, generally comprising a cyclone and a filter.

Generally, the equipment for atomizing or spraying the solution is a compressed gas sprayer or a dispersion turbine. Also ultrasounds nozzles can be used in present invention for spraying the solution.

The sodium bicarbonate solution is preferably an aqueous sodium bicarbonate solution. However, other polar solvents or mixtures of polar solvents, for example mixtures of water and ethanol, in which the additive is soluble may also be suitable. In this case an inert gas towards ethanol, such as carbon dioxide, or nitrogen is generally used in order to avoid gas combustion and/or gas explosion.

The present invention relates to a method for producing sodium bicarbonate particles by spray-drying of an aqueous solution comprising 1 to 10% by weight of sodium bicarbonate and an additive selected from the group consisting of: a compound of magnesium (Mg), sodium alkylbenzene sulfonate and soybean lecithin.

The compound of magnesium Mg is preferably a magnesium salt, more preferably it is a magnesium salt which water solubility is at least 5000 mg Mg/kg of water (5 g/kg). Magnesium compounds or magnesium salts such as: $MgCl_2$, $MgSO_4$, $MgNO_3$ are preferred. $MgCl_2$ is more preferred. In present invention when a quantitative proportion of magnesium compound additive is described, it relates to the quantity of the magnesium compound expressed in weight of magnesium Mg.

Alkylbenzene sulfonate in present invention is a benzenesulfonate with an alkyl chain comprising generally at least 6 carbons, preferably at least 8 carbons even more preferably at least 10 carbons. The alkyl chain comprises advantageously at most 24 carbons, preferably at most 20 carbons, even more preferably at most 16 carbons. Dodecylbenzene sulfonate is particularly advantageous. In present invention, the alkylbenzene sulfonate is generally used as its sodium salt.

The soybean lecithin used in the present invention is preferably the lecithin compound derived from soybean oil.

In the present invention, the additive is advantageously added in an amount of 1 to 1000 mg, or 1 to 2000 mg, of active material per kilogram of sodium bicarbonate solution. Generally the aqueous solution comprises at least 1 mg, preferably at least or more than 5 mg, more preferably at least or more than 10 mg, even more preferably at least or more than 100 mg, even more preferably at least or more than 200 mg of the additive per kilogram of aqueous solution, and when the additive is a magnesium compound the above quantities are expressed of mg Mg/kg of aqueous solution. Generally the aqueous solution comprises at most or less than 2000 mg, preferably at most or less than 1500 mg, more preferably at most or less than 1200 mg of the additive per kilogram of aqueous solution.

Generally the aqueous solution comprises at least or more than 2%, preferably at least or more than 3%, more preferably at least or more than 4%, and even more preferably at least 5% by weight of sodium bicarbonate. High concentration of sodium bicarbonate in the aqueous solution is detrimental as leading to high speed plugging of the spraying or atomizing device. Therefore it is generally recommended that the aqueous solution comprises at most or less than 10%, preferably at most or less than 8%, more preferably at most or less than 6% of sodium bicarbonate. Preferably, the sodium bicarbonate solution is an aqueous solution comprising 1% to 10%, advantageously 3% to 8%, more advantageously 4% to 6% by weight of sodium bicarbonate.

The drying with a hot gas breaks part of the sodium bicarbonate down into the form of sodium carbonate, $CO_2$ and water. In one advantageous embodiment of the present invention, the spray-drying is carried out in a gas comprising at least 5%, advantageously at least 10%, more advantageously at least 20% and even more advantageously at least 30% of $CO_2$ by volume on a dry gas basis. This enables to limit the sodium bicarbonate decomposition into sodium carbonate solid and $CO_2$ and water gasses.

Thus, a content with a $CO_2$ of 30% vol. makes it possible to reduce the sodium carbonate content of the sodium bicarbonate particles to less than 1% by weight.

In an even more advantageous embodiment of the invention, the spray-drying, or the atomization, is carried out in a gas comprising at least 80%, advantageously at least 90% and more advantageously at least 95% of CO2 by volume on a dry gas basis.

Generally, the spray-drying is carried out with a gas preheated between 40° C. and 220° C. Advantageously the spray-drying is carried out in a spray-drying chamber and wherein the gas is preheated before being introduced into the spray-drying chamber at at least 40°, preferably at at least 500, more preferably at at least 600, even more preferably at at least 70° C. Also advantageously, the gas is preheated before being introduced into the spray-drying chamber at at most 2200, preferably at at most 2000, more preferably at at most 1800, even more preferably at at most 130° C.

It is preferable for the temperature of the gas after the spray-drying operation to be at most 80° C., advantageously at most 70° C. and more advantageously at most 60° C.

In one embodiment of the invention, the aqueous solution is preheated to a temperature of at least 20° C. and preferably at at most 80° C. before being sprayed during the spray-drying operation. In one particular embodiment, the aqueous solution is preheated to a temperature of at least 20° C. and at most 25° C. before being sprayed during the spray-drying operation.

The invention also relates to sodium bicarbonate particles produced by the method according the present invention, and comprising at least 20 mg, preferably at least or more than 100 mg, more preferably at least or more than 500 mg, even more preferably at least or more than 5 000 mg, even more preferably at least or more than 10 000 mg of the additive per kg of sodium bicarbonate particles. The sodium bicarbonate particles of the invention comprises generally at most 50 000 mg, preferably at most 30 000 mg, more preferably at most 20 000 mg of the additive. In particular the invention also relates to sodium bicarbonate particles comprising from 20 to 20 000 mg of a magnesium salt, such as $MgCl_2$, $MgSO_4$ or $MgNO_3$ or of sodium dodecylbenzene sulfonate or of soybean lecithin, produced by the method according to the present invention.

The sodium bicarbonate particles obtained by the method of present invention have shown surprisingly increased BET specific surface area compared to sodium bicarbonate particles obtained without additives. This enables to produce high specific surface area sodium bicarbonate particles even using highly concentrated aqueous solution in spray drying. Moreover the size of such sodium bicarbonate particles are decreased compared to same particles obtained without additives. Also surprisingly, with such additives, generally at least a fraction of particles in spherical shape are obtained as observed with electron microscope. Statistical counting of such particles of spherical shapes can rise to at least 50% of obtained particles in spherical shape.numbers.

The present invention relates also to:
sodium bicarbonate particles obtainable by present process and having a BET specific surface area of at least 4 $m^2/g$, preferably of at least 5 $m^2/g$,
sodium bicarbonate particles obtainable by present process wherein the additive is a magnesium salt and having a BET specific surface area of at least 6 $m^2/g$, preferably of at least 9 $m^2/g$,
sodium bicarbonate particles obtainable by present process wherein the additive is a sodium alkylbenzenesulfonate and having a BET specific surface area of at least 6 $m^2/g$,
sodium bicarbonate particles obtainable by present process wherein the additive is soya lecithin or a sodium alkylbenzenesulfonate, and having a BET specific surface area of at least 4 $m^2/g$, preferably of at least 5 $m^2/g$.

These novel sodium bicarbonate particles have advantageous properties, such as:
a decreased particle size of sodium bicarbonate particles when magnesium salt or sodium alkylbenzene sulfonate or soya lecithin are used, with for instance a mean particle size by weight (D50) of about 3 to 11 μm, and particles that generally consist of individual crystallites of about 200 nm. By comparison sodium bicarbonate particles without additive have a mean particle size by weight (D50) of 13-14 μm,
increased BET specific surface area with values of up to about 6.6 $m^2/g$ when sodium alkylbenzene sulfonate is used, in particular sodium dodecylbenzene sulfonate; up to about 6 $m^2/g$ when soybean lecithin is used; and up to about 10 $m^2/g$ when $Mg^{2+}$ is used compared to BET specific surface area of 2.8 $m^2/g$ without additive in same conditions,
a spherical shape obtainable with magnesium salt or sodium alkylbenzene sulfonate or soybean lecithin as additive, allowing an improved fluidity of the powder close, in terms of angle of repose, for example, to bicarbonate of much larger sodium bicarbonate particle sizes, such as the ones of SOLVAY BICAR 0/13 (0-130 μm),
a consequent fraction of hollow spheres obtainable with magnesium salt,
an apparent bulk density of the powder consisting of particles of present invention of less than 450 $kg/m^3$, and in particular when a magnesium salt is used values down to about 200 $kg/m^3$ and even down to about 46 $kg/m^3$, compared with apparent weights generally of between 500 and 1200 $kg/m^3$ for the existing industrial products.
a high specific area of the sodium carbonate obtained by calcination of spray-dried sodium bicarbonate when sodium alkylbenzene sulfonate or soya lecithin are used (for instance about between 22 and 25 $m^2/g$).
a comparative slow dissolution speed into water when spray-dried sodium bicarbonate is produced with a magnesium salt (95% dissolution in at least 40 s) compared to 95% dissolution in at most 15 s for spray-dried sodium bicarbonate without any additive.

Furthermore, the low sized sodium bicarbonate particles of the invention, give a stable gel with water or polar solvents at low suspension densities: for example, 32-33% by weight of solid sodium bicarbonate in suspension in water, expressed relative to the total weight of the gel, in particular with sodium bicarbonate particles comprising magnesium.

This makes it possible to envisage various applications for these sodium bicarbonate particles, such as:
a blowing or foaming agent for polymers formed at temperatures between 110 et 180° C.: the speed of heat-debicarbonation of these sodium bicarbonate particles is very high: at 140° C., 95% of the solid matter is decomposed in 7 minutes, compared with 23 minutes a sodium bicarbonate of Bicar 0/13 type (Solvay) and 28 min for a Bicar 13/27 (Solvay); the particles comprising lecithin or sodium alkylbenzene sulfonate, in particular NaDBS, are particularly advantageous,
an exfoliating agent (healthcare): in particular the spherical shape can improve the effectiveness of the sodium bicarbonate particles enabling them to roll for longer on the skin, helping to remove dead cells,
anti-parasitic agents for the parasites of farm or domestic animals, such as poultry: used in gel form, silica is not needed in order to obtain a stable gel,
a deodorising agent (healthcare and household duties) by virtue of its high specific area and in particular its low organic matter content,
an inhalation agent (for pharmaceutical applications as an active-ingredient support) or for buffering the pH of the mucous membranes and of the lungs in the event of inhalation of acid gases.

Therefore, the present invention relates also to:
sodium bicarbonate particles obtainable or obtained by the process of present invention in shape of spheres,
sodium bicarbonate particles obtainable or obtained by the process of present invention wherein the additive is a magnesium salt, and in shape of hollow spheres.

In a particular the present invention relates to:
sodium bicarbonate particles with one of the above listed characteristics, obtainable or obtained with the process of present invention wherein the additive is a magnesium salt, and in shape of hollow spheres.
to sodium bicarbonate particles made with an aqueous composition comprising 150 to 500 mg of a magnesium salt expressed as mg of Mg per kg of aqueous solution, in particular wherein more than 70%, or more than 80%, or even more than 90% of the spheres are hollow spheres with a shape factor of less than 1, or also in another particular embodiment to such sodium bicarbonate particles having a bulk density of 40 to 80 kg/m$^3$.

The present invention relates also to:

sodium bicarbonate particles in shape of spheres obtained with present process wherein the aqueous solution comprises 100 to 1000 mg of sodium alkylbenzenesulfonate per kg of aqueous solution.

The present invention relates also to:

the use of sodium bicarbonate particles produced by the method of present invention, as blowing agent in foamed plastic production, the use of sodium bicarbonate particles produced by the method of present invention, in inhalable drug applications.

The present invention relates also to:

an aqueous gel comprising sodium bicarbonate particles produced by the method of present invention.

When sodium bicarbonate particles of present invention are calcined to sodium carbonate particles, they release water and carbon dioxide gas, according the following reaction:

$$2NaHCO_{3(s)} \rightarrow Na_2CO_{3(s)} + H_2O_{(g)} + CO_{2(g)}$$

When the sodium bicarbonate particles of the present invention are calcined, the BET specific surface area increases. Generally such particles comprise at least 60%, preferably at least 80% more preferably at least 90% by weight of sodium carbonate. Preferred calcining conditions such as temperature and calcination duration are such that at least 10%, preferably at least 20% and more preferably at least 40% of the additive remains in sodium carbonate particles (counted as Mg for compound of magnesium, and as organic carbon element for alkylbenzenesulfonate and for soybean lecithin).

In such conditions, the generated BET specific surface area of the sodium carbonate particles is increased compared to calcined sodium bicarbonate particles obtained by spray drying without additive. Moreover magnesium or carbon atoms from the additive added during spray drying and distributed partly in the volume and partly on the surface of sodium bicarbonate particles, remain in the volume and/or on the surface of the obtained calcined particles and are of interest when such calcined particles are the used as catalyser support or as active ingredient support in pharmaceutical applications.

Therefore present invention relates in particular to:

sodium carbonate particles obtained by calcination of sodium bicarbonate particles of present invention, sodium carbonate particles of present invention and having a BET specific surface area of at least 15 m$^2$/g, preferably of at least 20 m$^2$/g, sodium carbonate particles obtainable or obtained by calcination of sodium bicarbonate particles of present invention, comprising at least 10%, preferably at least 20% and more preferably at least 40% of the additive (counted as Mg for compound of magnesium, and as organic carbon element for alkylbenzenesulfonate and for soybean lecithin) obtainable or obtained from the calcination of sodium bicarbonate particles produced with at least 150 mg, or at least 500 mg of a magnesium salt (expressed as Mg) or of a sodium alkylbenzene sulfonate or soybean lecithin per kg of aqueous solution, sodium carbonate particles obtainable or obtained by calcination of sodium bicarbonate particles of present invention, preferably with obtainable or obtained sodium bicarbonate particles produced with at least 500 mg sodium alkylbenzene sulfonate or at least 500 mg soybean lecithin per kg of aqueous solution, in particular to sodium carbonate particles having a BET specific surface area of at least 15 m$^2$/g, preferably of at least 20 m$^2$/g, preferably with obtainable or obtained sodium bicarbonate particles produced with at least 500 mg sodium alkylbenzene sulfonate or at least 500 mg soybean lecithin per kg of aqueous solution, and more preferably also comprising at least 10%, more preferably at least 20% and even more preferably at least 40% of the additive in sodium carbonate particles (counted as Mg for compound of magnesium, and as organic carbon element for alkylbenzene and soybean lecithin).

The following examples are given by way of non-limiting illustration of the present invention, and variants thereof that are readily accessible to a person skilled in the art are possible.

EXAMPLES

The following examples were carried out with a BUCHI laboratory spray-dryer, model B-191.

The characteristics of the apparatus are given at Table 1.

TABLE 1 characteristics of used spray dryer

| Parameter | Operating conditions |
| --- | --- |
| Temperature of entering drying air | 20-220° C. |
| Flow rate of atomization compressed air | 400-800 l/h at 25° C. |
| Flow rate of entering air | 24-45 m$^3$/h at 25° C. |
| Flow rate of solution | Up to 27.8 g/min at 25° C. |
| Solute concentration | Solution saturated or unsaturated |
| Solution temperature | 20-80° C. |
| Type of solute | NaHCO$_3$ or Na$_2$CO$_3$ |
| Additives | With or without (reference test) |
| Type of additive | Mg compound, Alkylbenzensulfonate, Soybean lecithin |
| Additive concentration | 10, 100, 1000 ppm |
| [CO$_2$] | 0-76 vol % in the drying gas |

Example 1 (not in Compliance): Atomization Tests without Additive on Büchi B-191 Lab Spray-Dryer The test conditions are reproduced in Table 2.

TABLE 2

Reference test without additive

| Parameter | Value |
| --- | --- |
| Flow rate of drying air | 32 m$^3$/h at 20° C. |
| Temperature of exiting air | 50° C. |
| Flow rate of solution | 4.6 g/min |
| NaHCO$_3$ concentration | 50 g/kg solution |
| Solution temperature | 20-25° C. |
| Temperature of drying air | 95 +/− 3° C. |
| Flow rate of atomization compressed air | 600 l/h at 20° C. |

Sodium bicarbonate particles were obtained with the specific characteristics (mean of 4 reference tests performed: Ref. tests A, B, C, D):

BET specific surface area: 3.4 m²/g (+/−0.3)
Diameter D50: 9 m (−)
Free flow density: 216 kg/m3 (−)
Tapped density: 404 kg/m3 (−)
$Na_2CO_3$ content in powder: 4 w. % (+/−1%)

The weight-average diameter (D50) is measured by laser diffraction and scattering on a Malvern Mastersizer S particle size analyser using an He—Ne laser source having a wavelength of 632.8 nm and a diameter of 18 mm, a measurement cell equipped with a backscatter 300 mm lens (300 RF), an MS 17 liquid preparation unit, and an automatic solvent filtration kit ("ethanol kit") using ethanol saturated with bicarbonate.

The BET (Brunauer, Emmett and Teller) specific surface area was measured on a Micromeritics Gemini 2360 BET analyser using nitrogen as adsorbtive gas. The measure was realized on a powder sample presenting at least 1 m² of developed BET area, and was preliminary degassed with helium gas during 5 hours at ambient temperature (20 to 25° C.) in order to get rid of humidity traces adsorbed on the powder of sodium bicarbonate particles.

FIG. 1 shows a scanning microscope view of the sodium bicarbonate particles obtained for the reference test without additive.

Example 2 (in Compliance)

Tests with 1000 ppm of NaDBS as Additive (Ref Test 59)

The operating conditions were the same to those of Example 1, but with 1000 ppm of NaDBS in the sprayed solution.

Sodium bicarbonate particles were obtained with the specific characteristics:
BET specific surface area: 6 m²/g
$Na_2CO_3$ content in powder: 3.8%

The powder obtained was fluid, and the obtained particles were with spherical shape FIG. 2 shows a scanning microscope view of the sodium bicarbonate particles thus obtained with sodium alkylbenzenesulfonate (NaDBS) additive.

Example 3 (in Compliance)

Tests with 1000 ppm of Soybean Lecithin as Additive

The operating conditions were the same to those of Example 1, but with 1000 ppm of soybean lecithin in the sprayed solution.

Sodium bicarbonate particles were obtained with the specific characteristics:
BET specific surface area: 5.8 m²/g
$Na_2CO_3$ content in powder: 4.5%

The powder obtained was fluid, and the obtained particles were with spherical shape.

FIG. 3 shows a scanning microscope view of the sodium bicarbonate particles thus obtained with soybean lecithin additive.

Example 4 (in Compliance)

Tests with 100 and 1000 ppm of Mg as Additive ($MgCl_2$)

The operating conditions were the same to those of Example 1, but with 100 and 1000 ppm Mg in the sprayed solution.
Sodium bicarbonate particles were obtained with the respective specific characteristics (100 and 1000 ppm Mg):
BET specific surface area: 6.2 m²/g (100 ppm) and 9.7 m²/g (1000 ppm)
$Na_2CO_3$ content in powder: 5.7% (100 ppm) and 10.9% (1000 ppm)

Example 5 to 8 (in Compliance)

Test without additive, test with 1000 ppm of NaDBS; test with 1000 ppm of soya lecithin; test with 254 ppm of Mg as additive.

The operating conditions were the same to those of Example 1.

Table 3 and FIG. 4 to 7 detailed main properties on spray-dried sodium bicarbonate and SEM pictures thus obtained sodium bicarbonate particles.

TABLE 3

Results of lab tests with or without additive

| Sample with following additive | Mean Diameter (d50) μm | Bulk Density kg/m3 | Shape | BET specific surface m²/g | Shape factor a.PSE.d50/6 |
|---|---|---|---|---|---|
| Reference sodium bicarbonate (without additive) | 13-14 | 224-243 | Non uniform agglomerates | 3.4 | 1.4 to 2.4 |
| Sodium bicarbonate with SOLVAY RHODACAL DSB (NaDBS) | 6 | 400 | Sphere | 6.6 | 2.6 |
| Sodium bicarbonate with Soya lecithin | 5 | 405 | Sphere | 5.4 | 1.8 |
| Sodium bicarbonate with Magnesium chloride | 11 | 46 | Perfect Hollow Sphere with thin layer | 6 | 0.5 |

FIG. 4: Example 5—Ref test no additive: shows a scanning microscope view of the sodium bicarbonate particles thus obtained.

FIG. 5: Example 6: NaDBS as additive: shows a scanning microscope view of the sodium bicarbonate particles thus obtained.

FIG. 6: Example 7: Lecithin as additive: shows a scanning microscope view of the sodium bicarbonate particles thus obtained.

Figure 7:
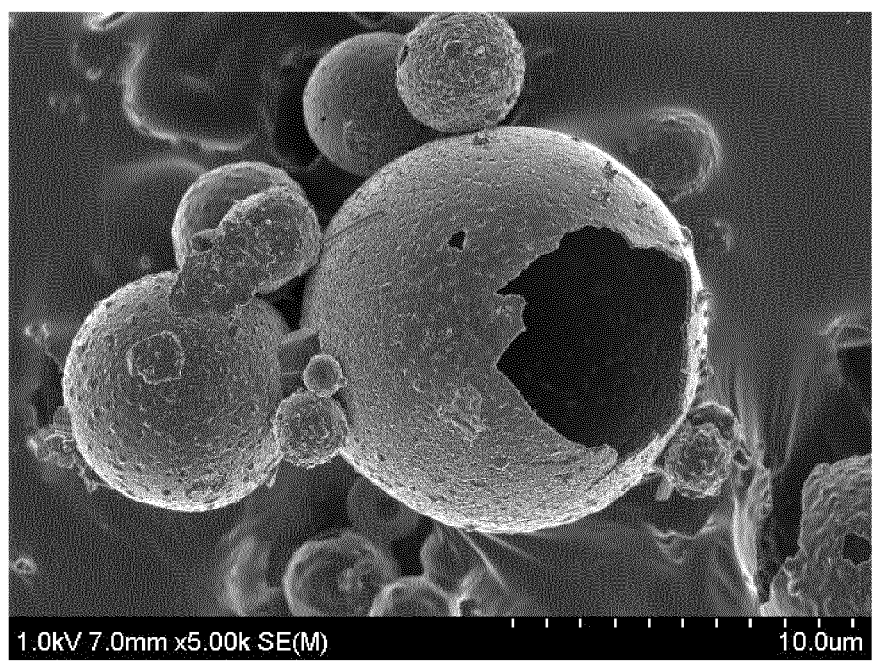
FIG. 7: is scanning microscope views of the sodium bicarbonate particles obtained at Example 8: Mg compound as additive.

FIG. 7: Example 8: Mg ions as additive: shows a scanning microscope view of the sodium bicarbonate particles thus obtained.

Similar tests were performed using $MgSO_4$, $Mg(NO_3)_2$ as above in same Mg quantities. Similar results were obtained.

We can note that the hollow spheres are obtained with intermediate amount of magnesium ions (see test at about 254 ppm Mg). If the concentration into the solution is high about 1000 ppm Mg, spheres explodes leading to very fine particles (such as in Example 4).

Figure 8:
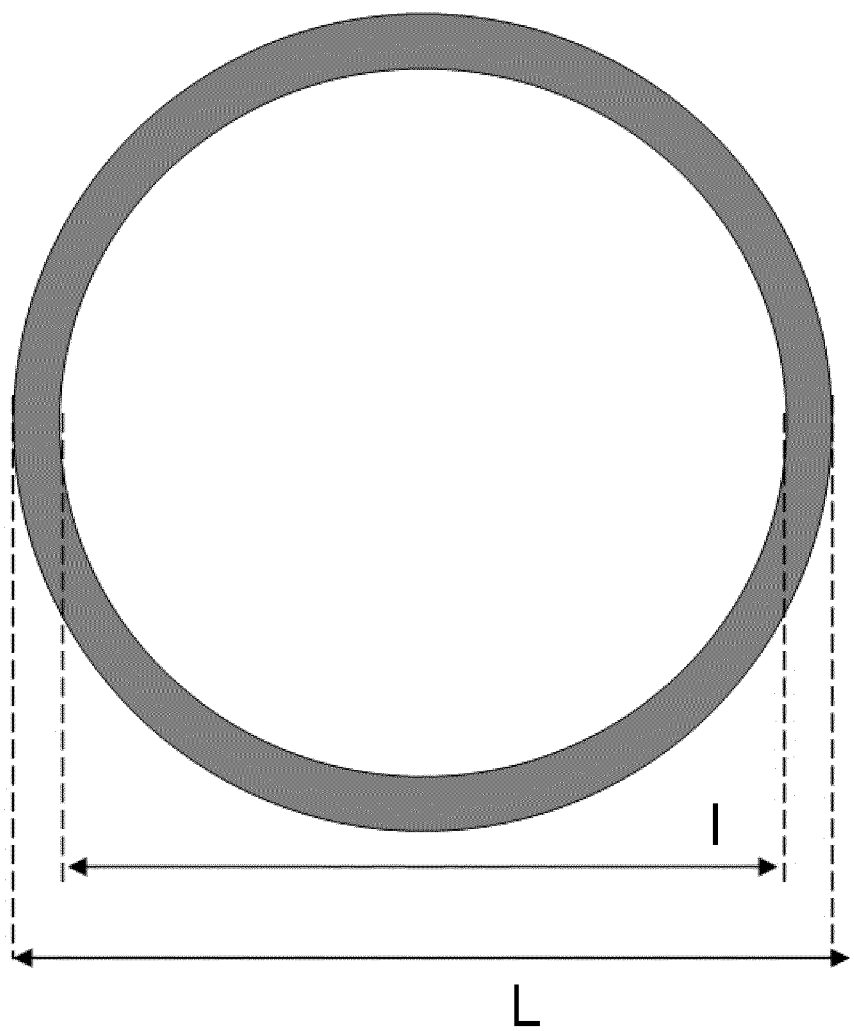
FIG. 8: is a schematic view (cut) of a sodium bicarbonate particle hollow sphere and formula notation of Examples 5-8.

Furthermore, a shape factor has been developed for assessing the ability of spheres to be hollow: this factor (noted gamma), links the specific area (noted a), the mean diameter D50 (noted L: corresponding to external diameter of an hollow sphere), the internal diameter of the hollow sphere (noted l), the thickness of the layer of the hollow sphere (therefore: noted L-l) and the bulk density (noted PSE) as follows:

FIG. 8: is a schematic view (cut) of a sodium bicarbonate particle hollow sphere With: $\gamma = \dfrac{L-l}{L}$;

$a = \dfrac{\pi(L^2 + l^2)}{\dfrac{4}{3}\rho\pi\left(\dfrac{L^3 - l^3}{8}\right)}$ and: $PSE = \dfrac{\dfrac{4}{3}\rho\pi\left(\dfrac{L^3 - l^3}{8}\right)}{\dfrac{4}{3}\pi\left(\dfrac{L^3}{8}\right)}$ Finally a shape factor can be defined as

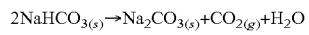

Shape Factor = : $\dfrac{a \times PSE \times d50}{6} = 1 + (1-\gamma)^2$

When the above shape factor is below 1, it indicates that the amount of hollow spheres into the spray-dried sodium bicarbonate is more than about 75%.

These sodium bicarbonate are further calcined in an oven at 240° C. during 2 h. The following chemical reaction occurs:

$2NaHCO_{3(s)} \rightarrow Na_2CO_{3(s)} + CO_{2(g)} + H_2O$

The reaction induces the generation of a high specific area sodium carbonate particles. About 25 m²/g with alkylbenzenesulfonate (NaDBS), 22 m²/g with Soya lecithin and 7 m²/g with magnesium compound.

TABLE 4

Specific area

| | BET specific surface area | | | |
|---|---|---|---|---|
| Sample with following additive | After production m²/g | 5 months later m²/g | % of BET decrease % | After calcination m²/g |
| Reference sodium bicarbonate (without additive) | 2.8 | 1.8 | 0.36 | 4 |
| Sodium bicarbonate with SOLVAY RHODACAL DSB (1000 ppm) | 6.6 | Not measured | — | 25 |
| Sodium bicarbonate with Soya lecithin (1000 ppm) | 5.4 | Not measured | — | 22 |
| Sodium bicarbonate with magnesium chloride (254 ppm Mg) | 6 | 2.9 | 0.52 | 7 |

Example 9 to 12 (in Compliance): Spray-Drying has Also been Tested at Larger Scale The air preheater consisted in four resistances allowing heating up the air at 300° C. The liquid was sprayed through a rotating atomizer (8 holes; 20 000 rev./min). The spray-drying chamber consisted of:
an upper cylinder of an internal diameter of 1 200 mm and a total height of about 2 times the internal diameter.
a cone at the bottom of the cylinder, with an angle of 60°.
The dried powder was recovered at the overflow of a cyclone (with cut size of about 2 μm) separating the wet air from the powder. Operating conditions are given at table 5.

Tests were performed: without additive, with 1000 ppm of NaDBS; with 1000 ppm of soya lecithin; test with 254 ppm of Mg as additive.

TABLE 5

Operating conditions on pilot plant

| Parameter | Value |
|---|---|
| Flow rate of drying air | Not measured |
| Temperature of drying air | 300° C. |
| Temperature of exiting air | 70° C. |
| Flow rate of solution | 20 kg/h |
| NaHCO₃ concentration | 75 g/kg |
| Solution temperature | Ambient (about 20° C.) |

Results of relative dissolution speed in water are listed at table 6. The test was performed in a beaker (diameter 100 mm, height/diameter: 1.7), equipped with four vertical blades stirrer total (diameter 42 mm and height 11 mm), filled with 1000 g of demineralized water. A magnetic stirring is set at 350 rev./min. The temperature of the liquid+solid mixture is set at 25° C. Then, 10 g of powder is quickly poured into the beaker and the dissolution is monitored through a conductivity measurement.

TABLE 6

| | Dissolution Time (s) | | |
|---|---|---|---|
| Samples | 1 | 2 | Mean value |
| Spray-dried Bicarbonate without additive | 10.5 | 10.6 | 11 |
| Bicar + MgCl₂ (Ref: 'fût1') | 40.3 | 53.7 | 47 |

Those results show that the dissolution time ($t_{95\%}$) of the obtained sodium bicarbonate particles produced with Mg compound, is sensitively increased compared to particles obtained without additive.

While preferred embodiments of this invention have been shown and described, modifications thereof can be made by one skilled in the art without departing from the spirit or teaching of this invention. The embodiments described herein are exemplary only and are not limiting. Many variations and modifications of systems and methods are possible and are within the scope of the invention.

Should the disclosure of any patents, patent applications, and publications which are incorporated herein by reference conflict with the description of the present application to the extent that it may render a term unclear, the present description shall take precedence.

The invention claimed is:
1. A method for producing sodium bicarbonate particles comprising:

spray-drying of an aqueous solution comprising 1 to 10% by weight of sodium bicarbonate and an additive selected from the group consisting of: a magnesium salt, sodium alkylbenzene sulfonate and soybean lecithin, to form sodium bicarbonate particles, wherein said formed sodium bicarbonate particles have a lower mean particle size D50 by weight compared to sodium bicarbonate particles obtained without the additive and at least 50% of the formed sodium bicarbonate particles have spherical shape, wherein said spray-drying is carried out in a gas comprising at least 5% of $CO_2$ by volume on a dry gas basis and in a spray-drying chamber, and wherein the gas is preheated before being introduced into the spray-drying chamber at a temperature of at least 40° C. and at most 220° C.

2. The method according to claim 1, wherein the aqueous solution comprises at least 1 mg and at most 2000 mg of the additive per kilogram of aqueous solution, and when the additive is a magnesium compound, the above quantities are expressed of mg Mg/kg of said aqueous solution.

3. The method according to claim 1, comprising at most 1500 mg of the additive per kilogram of said aqueous solution.

4. The method according to claim 1, wherein said aqueous solution comprises at least or more than 2% by weight of sodium bicarbonate.

5. The method according to claim 1, wherein said aqueous solution comprises at most or less than 8% of sodium bicarbonate.

6. The method according to claim 1, wherein the gas is preheated before being introduced into the spray-drying chamber at a temperature of at most 200° C.

7. The method according to claim 1, wherein said gas after spray-drying has a temperature of at most 80° C.

8. Sodium bicarbonate particles produced by the method according to claim 1, and comprising at least 20 mg and at most 50,000 mg of the additive per kg of sodium bicarbonate particles, wherein said sodium bicarbonate particles have a lower mean particle size D50 by weight compared to sodium bicarbonate particles obtained without the additive and at least 50% of the formed sodium bicarbonate particles have spherical shape and wherein the sodium bicarbonate particles have a bulk density of between 40 and less than 450 kg/m$^3$.

9. The sodium bicarbonate particles according to claim 8, having a BET specific surface area of at least 4 m$^2$/g.

10. The sodium bicarbonate particles according to claim 9, wherein the additive is a compound of magnesium $Mg^{2+}$ and having a BET specific surface area of at least 6 m$^2$/g.

11. The sodium bicarbonate particles according to claim 9, wherein the additive is an alkylbenzenesulfonate and having a BET specific surface area of at least 6 m$^2$/g.

12. The sodium bicarbonate particles according to claim 9, wherein the additive is soybean lecithin.

13. The sodium bicarbonate particles according to claim 8, wherein the additive is a magnesium salt, and being in shape of hollow spheres.

14. The sodium bicarbonate particles according to claim 8, being made with an aqueous composition comprising from 150 to 500 mg Mg of a magnesium salt per kg of aqueous solution.

15. The sodium bicarbonate particles according to claim 14, having a bulk density of 40 to 80 kg/m$^3$.

16. The sodium bicarbonate particles according to claim 8, being made with an aqueous solution comprising 100 to 1000 mg of sodium alkylbenzenesulfonate per kg of aqueous solution.

17. An aqueous gel comprising the sodium bicarbonate particles according to claim 8.

18. Sodium carbonate particles obtained by calcination of the sodium bicarbonate particles according to claim 8, and having a BET specific surface area of at least 15 m$^2$/g.

19. Sodium bicarbonate particles, comprising at least 20 mg and at most 50,000 mg of an additive per kg of sodium bicarbonate particles and having a BET specific surface area of at least 6 m$^2$/g, wherein the additive is a compound of magnesium $Mg^{2+}$, wherein said sodium bicarbonate particles have a lower mean particle size D50 by weight compared to sodium bicarbonate particles obtained without the additive and at least 50% of the formed sodium bicarbonate particles have spherical shape and wherein the sodium bicarbonate particles have a bulk density of from 40 to 80 kg/m$^3$.

20. The sodium bicarbonate particles according to claim 8, having a mean particle size by weight (D50) of about 3 to 11 μm.

21. The method according to claim 1, wherein said sodium bicarbonate particles have a mean particle size by weight (D50) of about 3 to 11 μm.

22. The sodium bicarbonate particles according to claim 19, wherein more than 70% of the spheres are hollow spheres with a shape factor of less than 1.

* * * * *